United States Patent
Sumida et al.

(10) Patent No.: US 6,943,271 B2
(45) Date of Patent: Sep. 13, 2005

(54) PROCESS FOR PRODUCING FLUORINE-CONTAINING, POLYMERIZABLE STYRENE MONOMER AND INTERMEDIATES USED IN SAME

(75) Inventors: Shinichi Sumida, Saitama (JP); Takashi Kume, Gainesville, FL (US); Sunao Koga, Saitama (JP); Haruhiko Komoriya, Saitama (JP)

(73) Assignee: Central Glass Company, Limited, Ube (JP)

( * ) Notice: Subject to any disclaimer, the term of this patent is extended or adjusted under 35 U.S.C. 154(b) by 95 days.

(21) Appl. No.: 10/600,510

(22) Filed: Jun. 23, 2003

(65) Prior Publication Data

US 2004/0002612 A1 Jan. 1, 2004

(30) Foreign Application Priority Data

Jun. 24, 2002 (JP) ........................................ 2002-183138

(51) Int. Cl.$^7$ ............................ C07C 41/08; C07F 7/02
(52) U.S. Cl. ...................... 568/659; 568/660; 568/661; 568/662; 568/663; 568/811; 568/812; 568/813; 568/814; 556/9; 556/12
(58) Field of Search ................. 568/659, 660, 568/661, 662, 663, 811, 812, 813, 814; 556/9, 12

(56) References Cited

U.S. PATENT DOCUMENTS 3,179,640 A * 4/1965 Middleton .................. 526/249
5,352,742 A * 10/1994 Han et al. .................... 525/276

FOREIGN PATENT DOCUMENTS

DE      42 07 261     3/1992

OTHER PUBLICATIONS

Fender, N. et al. "Characterization of New Aromatic Polymers for 157 nm Photoresist Applications", *Proceedings of SPIE–The International Society for Optical Engineering* (2001), vol. 4345, pp. 417–427.

* cited by examiner

Primary Examiner—Rosalynd Keys
(74) Attorney, Agent, or Firm—Crowell & Moring LLP

(57) ABSTRACT

A fluorine-containing styrene monomer of the formula (2) is produced by a first, second or third process. The first process includes (a) reacting a compound of the formula (1) with a compound of the formula (3), in the presence of a metal catalyst; (b) reacting the product of the step (a) with a base; and (c) reacting the product of the step (b) with hydrogen, in the presence of a metal catalyst and a phosphine or amine, thereby producing the target styrene monomer. The second process includes reacting a compound of the formula (1) with a compound of the formula (12), in the presence of a metal catalyst, thereby producing the target styrene monomer. The third process includes reacting a compound of the formula (13) with a compound of the formula (14) or (15), in the presence of a base, thereby producing the target styrene monomer.

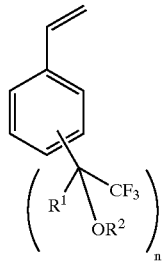

(2)

14 Claims, No Drawings

PROCESS FOR PRODUCING FLUORINE-CONTAINING, POLYMERIZABLE STYRENE MONOMER AND INTERMEDIATES USED IN SAME

BACKGROUND OF THE INVENTION

The present invention relates to a process for producing a fluorine-containing, polymerizable styrene monomer and to intermediates used in the process.

Aromatic polymers produced by polymerization or copolymerization of fluorine-containing styrene monomers are known to be important compounds as resist materials (see Fender. Nicolette et al., Proceedings of SPIE—The International Society for Optical Engineering (2001), vol. 4345, pp. 417–427).

There is known a process for producing a fluorine-containing styrene monomer, 4-(2-hydroxyhexafluoro-2-propyl)styrene, by the steps of (a) reacting 4-ethyl-1-(2-hydroxyhexafluoro-2-propyl)benzene with bromine under light irradiation to produce 1-(1-bromoethyl)-4-(2-hydroxyhexafluoro-2-propyl)benzene, (b) reacting the product of the step (a) with silver acetate to produce 1-(1-acetoxyethyl)-4-(2-hydroxyhexafluoro-2-propyl)benzene, and (c) pyrolyzing the product of the step (b) into the target product of this process, 4-(2-hydroxyhexafluoro-2-propyl)styrene. In this process, silver acetate used in the step (b) is a compound of high price. Furthermore, the pyrolysis of the step (c) may produce the target product with low yield and may be inferior in operation easiness. Thus, this process may be inferior as an industrial production process.

German Patent Application Publication 4207261 discloses a process for producing a fluorine-containing styrene monomer by the steps of (a) reacting 3-bromostyrene with metallic magnesium to produce a Grignard reagent and (b) reacting this Grignard reagent with hexafluoroacetone. This process may be difficult in controlling the reaction. Thus, this process may also be inferior as an industrial production process.

SUMMARY OF THE INVENTION

It is therefore an object of the present invention to provide a process for producing a fluorine-containing, polymerizable styrene monomer, which process is superior in industrially producing such styrene monomer.

According to the present invention, there is provided first, second and third processes for producing a fluorine-containing, polymerizable styrene monomer represented by the formula (2).

The first process includes the steps of:

(a) reacting a compound represented by the formula (1) with a compound represented by the formula (3), in the presence of a metal catalyst, thereby producing a compound represented by the formula (4);

(b) reacting the compound represented by the formula (4) with a base, thereby producing a compound represented by the formula (5); and (c) reacting the compound represented by the formula (5) with hydrogen, in the presence of a metal catalyst and one of a phosphine and an amine, thereby producing the fluorine-containing, polymerizable styrene monomer represented by the formula (2),

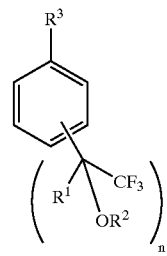

(1)

where $R^1$ a methyl group or trifluoromethyl group,
$R^2$ is a hydrogen atom, an alkyl group, or an aryl group, each of the alkyl group and the aryl group independently having a carbon atom number of 1 to 25, independently having a straight-chain, branched or ring form, and independently and optionally having at least one of a fluorine atom, an oxygen atom, and a carbonyl bond,
$R^3$ is a halogen atom or alkylsulfonyl group, and
n is 1 or 2,

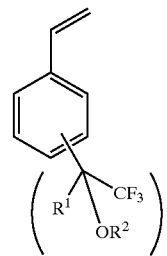

(2)

where $R^1$, $R^2$ and n respectively correspond to those of the formula (1),

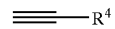

(3)

where $R^4$ is $C(OH)R^5R^6$ or $SiR^7R^8R^9$ where each of $R^5$ to $R^9$ independently has a carbon atom number of 1 to 25, independently is an alkyl group or aryl group, and independently and optionally has, in place of a carbon atom, at least one of a hetero atom and a substituent, and where each of $R^5$ and $R^6$ independently and optionally contains a fluorinated alkyl group,

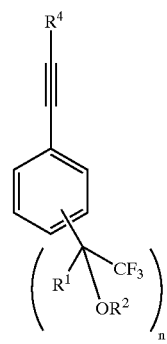

(4)

where $R^1$, $R^2$ and n respectively correspond to those of the formula (1), and $R^4$ corresponds to that of the formula (3), (5)

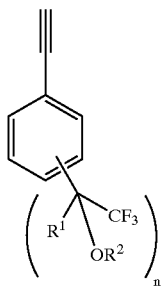

where $R^1$, $R^2$ and n respectively correspond to those of the formula (1).

The compound represented by the formula (4), which is the product of the step (a) of the first process, may be a novel compound represented by one of the formulas (6) to (9).

(6)

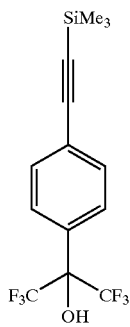

(7)

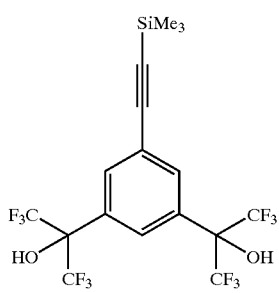

(8)

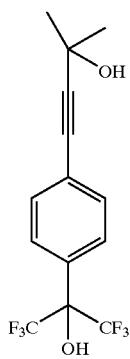

(9)

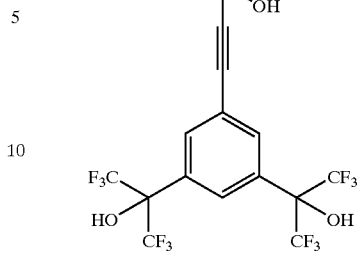

The compound represented by the formula (5), which is the product of the step (b) of the first process, may be a novel compound represented by the formula (10) or (11).

(10)

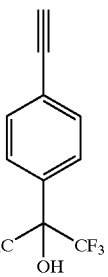

(11)

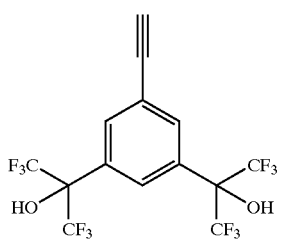

The second process includes the step of reacting a compound represented by the formula (1) with a compound represented by the formula (12), in the presence of a metal catalyst, thereby producing the fluorine-containing, polymerizable styrene monomer represented by the formula (2) where $R^1$, $R^2$ and n respectively correspond to those of the formula (1), (12)

$$\diagup\!\!\!\diagup R^{10}$$

where $R^{10}$ is a hydrogen atom, MgX, $SnR^{11}R^{12}R^{13}$, $SiR^{14}R^{15}R^{16}$, or $B(OR^{17})(OR^{18})$ where each of $R^{11}$ to $R^{18}$ independently has a carbon atom number of 1 to 25, independently is an alkyl group or aryl group, and independently and optionally has, in place of a carbon atom, at least one of a hetero atom and a substituent, and where X represents a halogen atom.

The third process includes the step of reacting a compound represented by the formula (13) with a compound represented by the formula (14) or (15), in the presence of a base, thereby producing the fluorine-containing, polymerizable styrene monomer represented by the formula (2) where $R^1$, $R^2$ and n respectively correspond to those of the formula (13),

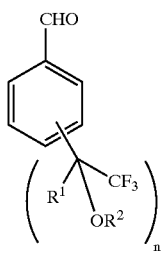

(13)

where $R^1$ a methyl group or trifluoromethyl group, $R^2$ is a hydrogen atom, an alkyl group, or an aryl group, each of the alkyl group and the aryl group independently having a carbon atom number of 1 to 25, independently having a straight-chain, branched or ring form, and independently and optionally having at least one of a fluorine atom, an oxygen atom, and a carbonyl bond, n is 1 or 2, $$R^{19}{}_3PCH_3X \qquad (14)$$

$$(R^{19}O)_3P(O)CH_3 \qquad (15)$$

where $R^{19}$ is a $C_{1-25}$ alkyl or aryl group and optionally has, in place of at least one carbon atom, at least one of a hetero atom and a substituent, and where X represents a halogen atom.

DESCRIPTION OF THE PREFERRED EMBODIMENTS

The first process of the present invention is described in detail as follows.

As stated above, the step (a) is conducted by reacting a compound of the formula (1) with a compound (an acetylene derivative) of the formula (3) in the presence of a metal catalyst, thereby producing a compound of the formula (4).

The group $R^1$ of the formula (1) is a methyl group or trifluoromethyl group. In order to achieve low refractive index and high transparency (particularly in the ultraviolet wavelength region), $R^1$ is preferably trifluoromethyl group.

The group $R^2$ of the formula (1) represents a hydrogen atom, an alkyl group, or an aryl group. Each of the alkyl group and the aryl group independently has a carbon atom number of 1 to 25, independently has a straight-chain, branched or ring form, and independently and optionally has at least one of a fluorine atom, an oxygen atom, and a carbonyl bond. Although the structure of $R^2$ is not particularly limited, it may be basically a hydrogen atom, which is the most simple in structure and is capable of providing high transparency. This hydrogen atom can be modified with a suitable substituent depending on the use of the resulting polymers. For example, the use of suitable substituents can provide the crosslinking property, the positive type photosensitivity (achieved by photoacid generator) and etching resistance for the purpose of having solubility in organic solvents and basic aqueous solutions, high glass transition point, and heat resistance in soldering.

The $C_1$–$C_{25}$ alkyl group used as $R^2$ may be selected from methyl group, ethyl group, isopropyl group, n-propyl group, sec-butyl group, cyclopropyl group, cyclopentyl group, cyclohexyl group, ethylhexyl group, norbornel group, and adamantyl group. The $C_1$–$C_{25}$ aryl group used as $R^2$ may be selected from phenyl group and 4-methoxybenzyl group. These alkyl and aryl groups may be groups in which hydrogen atoms have been partially or fully replaced with fluorine atoms, such as trifluoromethyl group, 2,2,2-trifluoromethylethyl group, and 1,1,1,3,3,3-hexafluoroisopropyl group. The group $R^2$ containing oxygen atom may be selected from linear ether groups (e.g., methoxymethyl ether and methoxyethoxymethyl ether) and cyclic ethers (e.g., tetrahydrofuran and tetrahydropyrane). Those having a carbonyl group may be selected from acetyl group, propionyl group, butyryl group, heptanoyl group, hexanoyl group, valeryl group, isovaleryl group, propylcarbonyl group, pivaloyl group, hexylcarbonyl group, cyclohexylcarbonyl group, tert-butoxycarbonyl group, and benzoyl group. Furthermore, these exemplary groups as $R^2$ may be ones in which hydrogen atoms have been partially or fully replaced with fluorine atoms.

The group $R^3$ of the formula (1) represents a halogen atom (e.g., fluorine atom, chlorine atom, and iodine atom) or alkylsulfonyl group (e.g., trifluoromethylsulfonyl group, methylsulfonyl group, p-tolylsulfonyl group, pentafluoroethylsulfonyl group, and nonafluorobutylsulfonyl group). Of these examples, bromine atom, iodine atom and trifluoromethylsulfonyl group are preferable.

The group $R^4$ of the formula (3) represents $C(OH)R^5R^6$ or $SiR^7R^8R^9$ where each of $R^5$ to $R^9$ independently has a carbon atom number of 1 to 25, independently is an alkyl group or aryl group, and independently and optionally has, in place of a carbon atom, at least one of a hetero atom and a substituent. This alkyl group may be selected from methyl group, ethyl group, isopropyl group, n-propyl group, n-butyl group, sec-butyl group, cyclopropyl group, cyclopentyl group, and cyclohexyl group. The aryl group may be selected from phenyl group and 4-methoxybenzyl group. Each of $R^5$ and $R^6$ may be a fluorinated alkyl group in which hydrogen atoms of the alkyl group have been partially or fully replaced with fluorine atoms, such as trifluoromethyl group, 2,2,2-trifluoromethylethyl group, and 1,1,1,2,2,2-hexafluoroisopropyl group. In the step (a) of the first process, the acetylene derivative of the formula (3) may be used in an amount of 1–10 moles, preferably 1–5 moles, more preferably 1–3 moles, per mol of the compound of the formula (1).

The metal catalyst used in the step (a) of the first process may be selected from copper complexes, iron complexes, cobalt complexes, nickel complexes, rhodium complexes, palladium complexes, ruthenium complexes, platinum complexes, and combinations of these complexes. In particular, the metal catalyst is preferably a combination of a palladium complex and a copper complex. These palladium and copper complexes used are not particularly limited. The palladium complex may be selected from bis(dibenzylideneacetone)palladium ($Pd(dba)_2$), tris(dibenzylidene)(chloroform)dipalladium ($Pd_2(dba)_3(CHCl_3)$), tetrakis(triphenylphosphine)palladium ($Pd(PPh_3)_4$), palladium acetate $Pd(OCOMe)_2$, $PdCl_2$, $PdBr_2$, $PdCl_2(PPh_3)_2$, $Pd(OCOMe)_2(PPh_3)_2$, $PdBr_2(PPh_3)_2$, $PdCl_2(PMe_3)_2$, $PdCl_2[P(Ph)_2CH_2CH_2P(Ph)_2]$, $PdCl_2[P(Ph)_2CH_2CH_2CH_2P(Ph)_2]$, $PdCl_2[P(Ph)_2CH_2CH_2CH_2CH_2P(Ph)_2]$, and $Pd_2Br_4(PPh_3)_2$, where Me and Ph represent methyl group and phenyl group, respectively. The copper complex may be a monovalent or bivalent copper salt. It is preferably a monovalent copper salt, such as copper iodide, copper bromide, copper chloride, and copper cyanide. The total amount of the palladium and copper complexes may be 0.00001–0.5 moles, preferably 0.00005–0.1 moles, more preferably 0.0001–0.1 moles, per mol of the compound of the formula (1). If it is less than 0.00001 moles, the reaction rate may become too slow, making the reaction disadvantageous to an industrial production. Although an amount greater than 0.5 moles does not cause particular problems in conducting the reaction, it may become uneconomical.

It is preferable to add a phosphine in the step (a) of the first process, since the palladium complex can be stabilized and thereby the reaction proceeds preferably. This phosphine may be selected from common phosphines, such as triphenylphosphine, tri-o-tolylphosphine, triethylphosphine, tri-n-butylphosphine, 1,1'-bis(diphenylphosphino)ferrocene (dppf), 1,4-bis(diphenylphosphino)butane, 1,3-bis (diphenylphosphino)propane, and 1,2-bis (diphenylphosphino)ethane. The phosphine used in the reaction may be in an amount of 10 moles or less, preferably 7 moles or less, more preferably 5 moles or less, per mol of the palladium complex. If it is greater than 10 moles, the reaction rate may become too slow. Furthermore, it may become uneconomical.

In case that a combination of a palladium complex and a copper complex is used as the metal catalyst of the step (a) of the first process, it is necessary to add a base to scavenge an acid that is generated by the reaction. Nonlimitative examples of this base are (1) inorganic bases such as sodium hydroxide, sodium carbonate, sodium hydrogencarbonate, potassium hydroxide, potassium carbonate, potassium hydrogencarbonate, sodium hydride, sodium methoxide, sodium ethoxide, sodium tert-butoxide, and potassium tert-butoxide; and (2) organic bases such as triethylamine, diethylamine, piperidine, pyrrolidine, and 1,8-diazabicyclo [5,4,0]-7-undecene. Of these, organic bases are preferable, and triethylamine and diethylamine are particularly preferable. The base may be in an amount of 1–100 moles, preferably 1–10 moles, per mol of the compound of the formula (3).

The step (a) of the first process can be conducted in a solvent, as long as it is inert to the reaction. Its nonlimitative examples are hydrocarbons (e.g., hexane and benzene), ethers (e.g., diethyl ether, tetrahydrofuran, and dioxane), halogenated hydrocarbons (e.g., dichloromethane and chloroform), alkyl ketones (e.g., acetone), alcohols (e.g., methanol and ethanol), and aprotic polar solvents (e.g., acetonitrile, N,N-dimethylformamide, dimethylsulfoxide, and hexamethylphosphoric triamide). These solvents may be used alone or in combination of at least two. The above-mentioned base (such as pyridine, triethylamine, diethylamine, piperidine, and pyrrolidine) can be used as the solvent, too.

Although the reaction temperature of the step (a) of the first process is not particularly limited, it may be from 0 to 200° C., preferably from room temperature to 150° C. The post-treatment after the reaction of the step (a) is not particularly limited. For example, it is possible to isolate the target product of the step (a) by adding the reaction liquid to water or iced water, followed by extraction with organic solvent. Another exemplary post-treatment is flash distillation.

The step (a) of the first process can be conducted by reacting a compound of the formula (16) with trimethylsilylacetylene in the presence of a metal catalyst, thereby producing a compound of the above formula (6). The replacement of a compound of the formula (16) in this reaction by a compound of the formula (17) produces a compound of the above formula (7). Furthermore, it can be conducted by reacting a compound of the formula (16) with 2-methyl-2-hydroxy-3-butyne in the presence of metal catalyst, thereby producing a compound of the above formula (8). The replacement of a compound of the formula (16) in this reaction by a compound of the formula (17) produces a compound of the above formula (9).

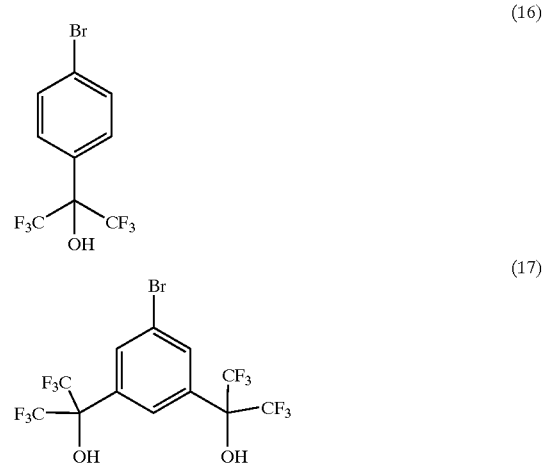

The step (b) of the first process is conducted by reacting the compound of the formula (4) (i.e., the product of the step (a)) with a base, thereby producing a compound of the formula (5). This base may be selected from the same examples as those of the above-mentioned base of the step (a). The base of the step (b) may be in an amount of 3–10 moles, preferably 3–5 moles, per mol of the compound of the formula (4).

The step (b) may be conduced in a solvent, as long as it is inert to the reaction. It may be selected from the same examples as those of the above-mentioned solvent of the step (a). It is preferably an alcohol (e.g., methanol and ethanol).

Although the reaction temperature of the step (b) of the first process is not particularly limited, it may be from 0 to 100° C., preferably from 20 to 80° C., more preferably from 20 to 50° C. Although the post-treatment after the reaction of the step (b) is not particularly limited, it may be conducted in the same way as that after the step (a).

The step (b) of the first process can be conducted by reacting a compound of the formula (6) or (8) with a base, thereby producing a compound of the formula (10). Furthermore, it can be conducted by reacting a compound of the formula (7) or (9) with a base, thereby producing a compound of the formula (11).

The step (c) of the first process is conducted by reacting the compound of the formula (5) with hydrogen, in the presence of a metal catalyst and one of a phosphine and an amine, thereby producing the fluorine-containing, polymerizable styrene monomer of the formula (2).

The metal catalyst of the step (c) is not particularly limited. Its examples are palladium catalysts (e.g., palladium-carbon, palladium-alumina, palladium-asbestos, palladium-barium carbonate, palladium-barium sulfate, palladium black, and palladium-calcium carbonate), platinum catalysts (e.g., platinum-carbon, platinum black, and platinum-carbonate), rhodium catalysts, ruthenium catalysts, and nickel catalysts (e.g., Raney nickel). Of these, palladium-barium sulfate and palladium-calcium carbonate are preferable. The amount of the metal catalyst is preferably 0.1 to 10 wt %, based on the total weight of the compound of the formula (5).

It is necessary in the step (c) to add a phosphine or an amine in order to improve selectivity of the reaction by lowering the production of overly reduced compounds. The phosphine may be triphenylphosphine or tributylphosphine, and the amine may be quinoline or diethylamine. The phosphine or amine may be in an amount of 0.1–50 wt %, based on the total weight of the metal catalyst.

The hydrogen pressure for conducting the step (c) may be from normal pressure (e.g. atmospheric pressure) to 100 atmospheres, preferably from normal pressure to 10 atmospheres. The reaction temperature of the step (c) may be 0 to 100° C., preferably from room temperature to 50° C. Since the reaction of the step (c) is a gas-liquid reaction, the gas-liquid contact efficiency has a great influence on the reaction rate. Therefore, it is preferable to use a reaction apparatus to improve the gas-liquid contact efficiency. For example, it is preferable to sufficiently stir the reaction liquid during the reaction.

The step (c) may be conducted in a solvent. This solvent is not particularly limited, and may be selected from alcohols (e.g., methanol, ethanol, isopropyl alcohol, butanol, and tert-butyl alcohol), ethers (e.g., tetrahydrofuran, diethyl ether, and 1,2-dimethoxyethane), and aromatic hydrocarbons (e.g., toluene and benzene).

The second process of the present invention is described in detail as follows.

As stated above, the second process includes the step of reacting a compound of the formula (1) with a compound of the formula (12), in the presence of a metal catalyst, thereby producing the fluorine-containing, polymerizable styrene monomer represented by the formula (2) where $R^1$, $R^2$ and n respectively correspond to those of the formula (1).

In the second process, the group $R^3$ of the formula (1) may be selected from the same exemplary halogen atoms and alkylsulfonyl groups as those of $R^3$ of the first process. Of these examples, bromine atom, iodine atom and trifluoromethylsulfonyl group are also preferable.

As stated above, the group $R^{10}$ of the formula (12) is a hydrogen atom, MgX, $SnR^{11}R^{12}R^{13}$, $SiR^{14}R^{15}R^{16}$, or $B(OR^{17})(OR^{18})$ where each of $R^{11}$ to $R^{18}$ independently has a carbon atom number of 1 to 25, independently is an alkyl group or aryl group, and independently and optionally has, in place of a carbon atom, at least one of a hetero atom and a substituent, and where X represents a halogen atom. Examples of the alkyl group for $R^{11}$ to $R^{18}$ are methyl group, ethyl group, isopropyl group, n-propyl group, n-butyl group, sec-butyl group, cyclopropyl group, cyclopentyl group, and cyclohexyl group. Examples of the aryl group for $R^{11}$ to $R^{18}$ are phenyl group and 4-methoxybenzyl group. The vinyl compound of the formula (12) may be in an amount of 1–10 moles, preferably 1–5 moles, more preferably 1–3 moles, per mol of the compound of the formula (1).

The metal catalyst used in the second process may be selected from iron complexes, cobalt complexes, nickel complexes, rhodium complexes, palladium complexes, ruthenium complexes, and platinum complexes. In particular, palladium complexes and nickel complexes are preferable. These palladium and nickel complexes usable in the second process are not particularly limited. The palladium complex may be selected from the same examples as those of the step (a) of the first process. The nickel complex may be selected from $NiCl_2$, $NiBr_2$, $NiCl_2(PPh_3)_2$, $NiBr_2(PPh_3)_2$, $NiCl_2[P(Ph)_2CH_2CH_2P(Ph)_2]$, and $NiCl_2[P(Ph)_2CH_2CH_2CH_2P(Ph)_2]$. The palladium or nickel complex may be in an amount of 0.001–0.1 moles, preferably 0.005–0.1 moles, more preferably 0.01–0.1 moles, per mol of the compound of the formula (1). If it is less than 0.001 moles, the reaction rate may become too slow, making the reaction disadvantageous to an industrial production. Although an amount greater than 0.1 moles does not cause particular problems in conducting the reaction, it may become uneconomical.

In the second process, it is preferable to add a phosphine in order to stabilize the metal complex and thereby make the reaction proceed well. This phosphine may be selected from common phosphines, such as those in the step (a) of the first process. The phosphine used in the reaction may be in an amount of 10 moles or less, preferably 7 moles or less, more preferably 5 moles or less, per mol of the palladium complex. If it is greater than 10 moles, the reaction rate may become too slow. Furthermore, it may become uneconomical.

The second process can be conducted in a solvent, as long as it is inert to the reaction. It may be selected from the same examples as those in the step (a) of the first process. In case that a Grignard reagent is used in the second process, it is preferable to use an ether solvent for the purpose of stabilizing the Grignard reagent.

In case that the group $R^{10}$ of the formula (12) is a hydrogen atom or $B(OR^{17})(OR^{18})$, it is necessary to conduct the second process in the presence of a base. This base is not particularly limited, and may be selected from inorganic bases (e.g., potassium acetate, sodium acetate, sodium hydroxide, potassium hydroxide, sodium carbonate, and potassium carbonate) and organic bases (e.g., triethylamine, tripropylamine, tri-o-octylamine, triallylamine, pyridine, and N,N-dimethylaniline). The base may be in an amount of 1–10 moles, preferably 1–5 moles, more preferably 1–3 moles, per mol of the compound of the formula (12). If it is less than 1 mole, the reaction may not proceed sufficiently, thereby lowering yield. Even if it exceeds 10 moles, yield of the target product may not improve further. In this case, the unreacted base remains in the system, making it economically disadvantageous.

In case that the group $R^{10}$ of the formula (12) is $SiR^{14}R^{15}R^{16}$, it is necessary to conduct the second process in the presence of a nucleophilic reagent. This nucleophilic reagent may be selected from (1) onium fluorides (e.g., tris(diethylamino)sulfonium difluorotrimethylsilicate, tris(dimethylamino)sulfonium difluorotrimethylsilicate, tris(dimethylamino) sulfonium bifluoride, tetrabutylammonium fluoride, tetrabutylammonium bifluoride, and benzyltrimethylammonium fluoride), (2) metal fluorides (e.g., cesium fluoride, potassium fluoride, and sodium fluoride), and (3) amines (e.g., triethylamine, diethylamine, ethylamine, tripropylamine, dipropylamine, dibutylamine, diisopropylamine, ethylduisopropylamine, morpholine, pyridine, and aniline). These compounds may be used alone or in mixture. The nucleophilic reagent may be used in a catalytic or excessive amount, relative to that of the compound of the formula (12).

Although the reaction of the second process may be conducted in the air, it is preferably conducted under an inert gas (e.g., nitrogen, helium and argon) atmosphere. The reaction temperature of the second process may be from 0 to 200° C., preferably 25–250° C. The reaction time may be 1 to 50 hr. Since the reaction time may vary depending on the raw material substrates and the reaction conditions, it is preferable to conduct the reaction, while checking the reaction progress by gas chromatography or NMR. Although the post-treatment after the reaction of the second process is not particularly limited, it may be conducted in the same way as that after the step (a) of the first process.

The reaction of the third process can be conducted by the sequential steps of:

(a) treating the compound of the formula (14) or (15) with a base in a solvent, thereby generating carbanion; and (b) adding the compound of the formula (13) to the product of the step (a) to conduct a condensation between the carbanion and the compound of the formula (13), thereby producing the fluorine-containing, polymerizable styrene monomer of the formula (2).

As stated above, $R^{19}$ of the formulas (14) and (15) is a $C_{1-25}$ alkyl or aryl group and optionally has, in place of at least one carbon atom, at least one of a hetero atom(s) and a substituent(s). This $C_{1-25}$ alkyl group may be selected from methyl group, ethyl group, isopropyl group, n-propyl group, n-butyl group, sec-butyl group, cyclopropyl group, cyclopentyl group, and cyclohexyl group. The $C_1$–$C_{25}$ aryl group may be selected from phenyl group and 4-methoxybenzyl group. The compound of the formula (14) or (15) may be in an amount of 1–10 moles, preferably 1–5 moles, more preferably 1–3 moles, per mol of the compound of the formula (13).

In the step (a) of the third process, the combination of the base and the solvent may be selected from (a) sodium hydroxide and water, (b) sodium carbonate and water, (c) potassium carbonate and water, (d) sodium ethoxide and ethanol or dimethylformamide, (e) sodium methoxide and a methanol-diethyl ether mixture or dimethylformamide, (f) triethylamine and ethanol or diglyme or chloroform or nitromethane, (g) pyridine and methylene chloride or nitromethane, (h) 1,5-diazabicyclo[4.3.0]non-5-ene and dimethylsulfoxide, (i) potassium t-butoxide and dimethylsulfoxide or tetrahydrofuran or benzene or dimethylformamide, (j) phenyl lithium and diethyl ether or tetrahydrofuran, (k) sodium amide and ammonia, and (l) sodium hydride and dimethylformamide or tetrahydrofuran.

Although the reaction temperature of the third process is not particularly limited, it may be from −50 to +100° C., preferably −30 to +80° C., more preferably 0 to +50° C. Although the post-treatment after the reaction of the third process is not particularly limited, it may be conducted in the same way as that after the step (a) of the first process.

The following nonlimitative examples are illustrative of the present invention. Examples 1–2, 3–7 and 8 are respectively illustrative of the first, second and third processes of the present invention.

EXAMPLE 1

In this example, the target product, 4-HFA-ST (18), was produced by the after-mentioned steps (a), (b) and (c) of the first process, as shown by the following reaction scheme.

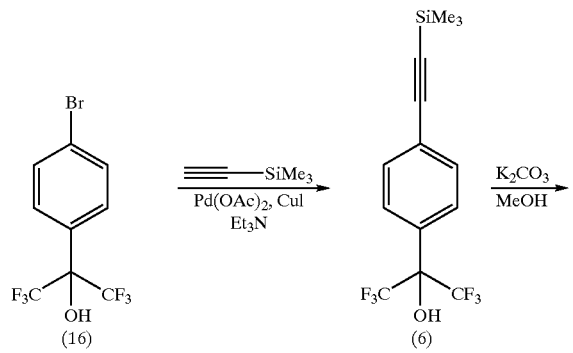

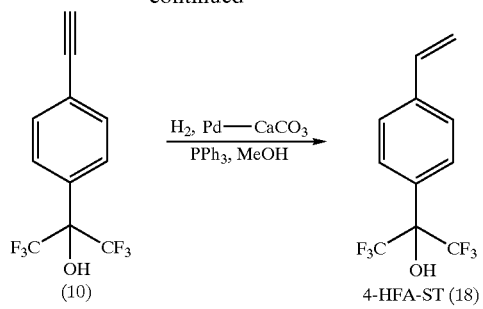

The step (a), trimethylsilylacetylation, was conducted as follows. At first, a three-necked flask (equipped with a reflux condenser and a stirrer) was charged under nitrogen atmosphere with 0.15 g (0.67 mmol) of palladium acetate (Pd $(OAc)_2$), 0.74 g (2.82 mmol) of triphenylphosphine ($PPh_3$) and 0.15 g (0.79 mmol) of cuprous iodide (CuI). Then, 50 ml of a triethylamine ($Et_3N$) solution (containing 21.7 g (67.2 mmol) of a compound of the formula (16)) and 10 ml of a triethylamine ($Et_3N$) solution (containing 7.26 g (73.9 mmol) of trimethylsilylacetylene) were sequentially added to the flask, followed by heating with an oil bath of 100° C. to conduct the reaction. After the reaction, the catalyst was removed by vacuum filtration. The resulting filtrate was concentrated by an evaporator. The obtained concentrate was transferred into a separating funnel, and hydrochloric acid was added thereto. The resulting aqueous layer was extracted several times with hexane. The resulting organic layers were combined together and washed with water and saturated brine. The obtained organic layer was dried by adding magnesium sulfate. Then, magnesium sulfate was removed from the organic layer by filtration, followed by vacuum distillation, thereby obtaining 17.1 g of a compound of the formula (6) (yield: 75%). This compound was found to have the following characteristics.

Boiling Point: 84–87° C./2 mmHg $^1$H-NMR ($CDCl_3$, TMS): 0.07 (9H,s), 3.23 (1H, brs), 7.35 (2H, d, J=8.0 Hz), 7.46 (2H, d, J=8.0 Hz)

The step (b), detrimethylsilylation, was conducted as follows. At first, a three-necked flask (equipped with a dropping funnel and a stirrer) was charged with 5.6 g (40.5 mmol) of potassium carbonate ($K_2CO_3$) and 15 ml of methanol (MeOH). While the flask was cooled with ice, 15 ml of a methanol solution (containing 11.6 g (34.1 mmol) of the compound of the formula (6) obtained by the step (a)) were added to the flask in a dropwise manner, followed by stirring at room temperature to conduct the reaction. After the reaction, the potassium carbonate was removed by vacuum filtration. The resulting filtrate was concentrated by an evaporator. The residue was transferred into a separating funnel, and hydrochloric acid was added thereto. The resulting aqueous layer was extracted with hexane. The resulting organic layers were combined together and washed with water and saturated brine. The obtained organic layer was dried by adding magnesium sulfate. Then, magnesium sulfate was removed from the organic layer by filtration, followed by vacuum distillation, thereby obtaining 7.4 g of a compound of the formula (10) (yield: 81%). This compound was found to have the following characteristics.

Boiling Point: 68–69° C./2 mmHg $^1$H-NMR (TMS, $CDCl_3$): 3.16 (1H, s), 3.48 (1H, s), 7.57 (2H, d, J=8.0 Hz), 7.68 (2H, d, J=8.4Hz).

The step (c), partial reduction, was conducted as follows. At first, a three-necked flask equipped with a stirrer was charged with 0.5 g of Lindlar catalyst (Pd—CaCO$_3$) and 2.5 g of triphenylphosphine (PPh$_3$). Then, 350 ml of a methanol (MeOH) solution (containing 50 g (0.19 mol) of the compound of the formula (10) obtained by the step (b)) were added to the flask. Then, while hydrogen (H$_2$) was introduced, the reaction mixture was stirred at room temperature to conduct the reaction. After the reaction, the catalyst was removed by filtration. The resulting filtrate was concentrated by an evaporator, followed by vacuum distillation, thereby obtaining 43.1 g of a compound of the formula (18) (yield: 86%). This compound was found to have the following characteristics.

$^1$H-NMR (TMS, CDCl$_3$): 3.44 (1H, s), 5.33 (1H, d, J=10.8 Hz), 5.81 (1H, d, J=17.6 Hz), 6.72 (1H, dd, J=17.6, 10.8 Hz), 7.46 (2H, d, J=8.0 Hz), 7.68 (2H, d, J=8.4 Hz)

EXAMPLE 2

In this example, the target product, 3,5-HFA-ST (19), was produced by the after-mentioned steps (a), (b) and (c) of the first process, as shown by the following reaction scheme. In fact, an intermediate represented by the formula (10) was produced by the two routes of the reaction scheme, as described as follows.

mmol) of palladium acetate (Pd(OAc)$_2$), 5.63 g (21.5 mmol) of triphenylphosphine (PPh$_3$) and 1.15 g (6.04 mmol) of cuprous iodide (CuI). Then, 2-liters of a triethylamine (Et$_3$N) solution (containing 250 g (0.51 mol) of a compound of the formula (17)) and 500 ml of a triethylamine solution (containing 55.9 g (0.57 mol) of trimethylsilylacetylene) were sequentially added to the flask, followed by heating with an oil bath of 100° C. to conduct the reaction. After the reaction, the catalyst was removed by vacuum filtration. The resulting filtrate was concentrated by an evaporator. The obtained concentrate was transferred into a separating funnel, and hydrochloric acid was added thereto. The resulting aqueous layer was extracted several times with ether. The resulting organic layers were combined together and washed with water and saturated brine. The obtained organic layer was dried by adding magnesium sulfate. Then, magnesium sulfate was removed from the organic layer by filtration, followed by vacuum distillation, thereby obtaining 204 g of a compound of the formula (7) (yield: 79%). This compound was found to have the following characteristics.

Boiling Point: 200° C./220Pa $^1$H-NMR (CDCl$_3$, TMS): 0.28 (9H,s), 3.65 (2H, s), 7.92 (2H, s), 8.04 (1H, s)

The step (b), detrimethylsilylation, was conducted to produce the compound of the formula (10) from the com-

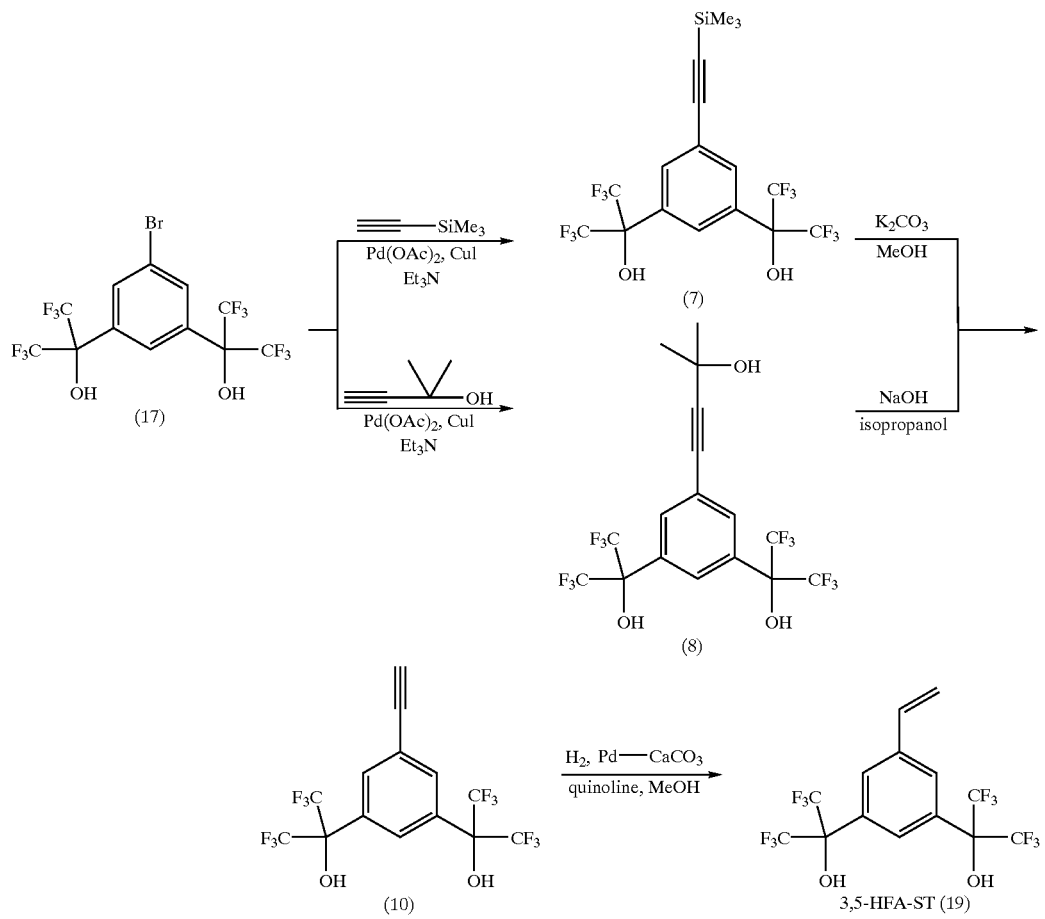

The step (a), trimethylsilylacetylation, for producing a compound of the formula (7) from a compound of the formula (17) was conducted as follows. At first, a three-necked flask (equipped with a reflux condenser and a stirrer) was charged under nitrogen atmosphere with 1.15 g (5.12 pound of the formula (7), as follows. At first, a three-necked flask (equipped with a dropping funnel and a stirrer) was charged with 122.6 g (0.89 mol) of potassium carbonate (K$_2$CO$_3$) and 113 ml of methanol (MeOH). While the flask was cooled with ice, 500 ml of a methanol solution containing 204 g (0.4 mol) of the compound of the formula (7) were added to the flask in a dropwise manner, followed by stirring at room temperature to conduct the reaction. After the reaction, the potassium carbonate was removed by filtration. The resulting filtrate was concentrated by an evaporator. The residue was transferred into a separating funnel, and hydrochloric acid was added thereto. The resulting aqueous layer was extracted with ether. The resulting organic layers were combined together and washed with water and saturated brine. The obtained organic layer was dried by adding magnesium sulfate. Then, magnesium sulfate was removed from the organic layer by filtration, followed by vacuum distillation, thereby obtaining 144 g of a compound of the formula (10) (yield: 82%). This compound was found to have the following characteristics.

Boiling Point: 78–79° C./185Pa $^1$H-NMR (TMS, CDCl$_3$): 3.20 (1H, s), 3.62 (2H, s), 7.96 (2H, s), 8.09 (1H, s)

The step (a), methylhydroxybutynylation, for producing a compound of the formula (8) from a compound of the formula (17) was conducted as follows. At first, a three-necked flask (equipped with a reflux condenser and a stirrer) was charged under nitrogen atmosphere with 0.17 g (0.74 mmol) of palladium acetate (Pd(OAc)$_2$), 0.82 g (3.1 mmol) of triphenylphosphine (PPh$_3$) and 0.17 g (0.88 mmol) of cuprous iodide (CuI). Then, 200 ml of a triethylamine (Et$_3$N) solution (containing 36.3 g (74.2 mmol) of a compound of the formula (17)) and 163 ml of a triethylamine solution (containing 7.49 g (89.0 mmol) of methylhydroxybutyne) were sequentially added to the flask, followed by heating with an oil bath of 100° C. to conduct the reaction. After the reaction, the catalyst was removed by vacuum filtration. The resulting filtrate was concentrated by an evaporator. The obtained concentrate was transferred into a separating funnel, and hydrochloric acid was added thereto. The resulting aqueous layer was extracted several times with ether. The resulting organic layers were combined together and washed with water and saturated brine. The resulting organic layer was dried by adding magnesium sulfate. Then, magnesium sulfate was removed from the organic layer by filtration, followed by vacuum distillation, thereby obtaining 31.4 g of a compound of the formula (8) (yield: 86%). This compound was found to have the following characteristics.

$^1$H-NMR (CDCl$_3$, TMS): 1.43 (6H, s), 2.78 (3H, brs), 7.80 (2H, s), 8.06 (1H, s)

The step (b), an elimination reaction, was conducted to produce the compound of the formula (10) from the compound of the formula (8), as follows. At first, a three-necked flask (equipped with a dropping funnel and a stirrer) was charged with 15 g (0.38 mol) of sodium hydroxide (NaOH) and 300 ml of an isopropanol solution containing 37.1 g (75.5 mmol) of a compound of the formula (8), followed by reflux. After the reaction, the residue was transferred into a separating funnel, and hydrochloric acid was added thereto. The resulting aqueous layer was extracted with ether. The resulting organic layers were combined together and washed with water and saturated brine. The obtained organic layer was dried by adding magnesium sulfate. Then, magnesium sulfate was removed by filtration, followed by vacuum distillation, thereby obtaining 23.3 g of a compound of the formula (10) (yield: 71%).

The step (c), a partial reduction, was conducted to produce a compound of the formula (19) from a compound of the formula (10), as follows. Under nitrogen atmosphere, a three-necked flask equipped with a stirrer was charged with 0.12 g of Lindlar catalyst (Pd—CaCO$_3$) and 1.2 g of quinoline. Then, 840 ml of a methanol (MeOH) solution containing 120 g (0.28 mol) of the compound of the formula (10) were added to the flask. Then, while hydrogen (H$_2$) was introduced, the reaction mixture was stirred at room temperature to conduct the reaction. After the reaction, the catalyst was removed by filtration. The resulting filtrate was concentrated by an evaporator. The resulting residue was transferred into a separating funnel, and hydrochloric acid was added thereto. The resulting aqueous layer was extracted with tert-butyl ether. The resulting organic layers were combined together and washed with water and saturated brine. The obtained organic layer was dried by adding magnesium sulfate. Then, magnesium sulfate was removed by filtration, followed by vacuum distillation, thereby obtaining 100 g of a compound of the formula (19) (yield: 83%). This compound was found to have the following characteristics.

$^1$H-NMR (TMS, CDCl$_3$): 3.56 (1H, s), 5.40 (1H, d, J=11.2 Hz), 5.85 (1H, d, J=17.6 Hz), 6.76 (1H, dd, J=17.6, 11.2 Hz), 7.84 (2H, s), 7.96 (1H, s)

EXAMPLE 3

In this example, the second process was conducted to produce the target product, 4-HFA-ST (18), as shown by the following reaction scheme.

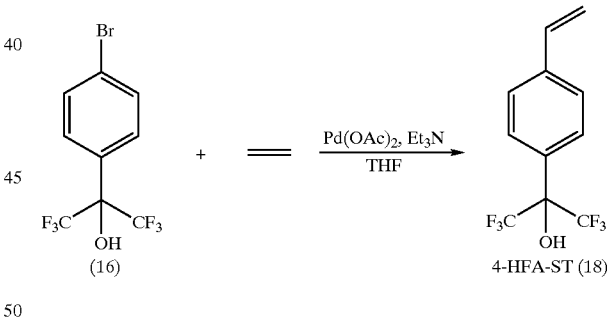

At first, an autoclave was charged with 32.3 g (0.1 mol) of a compound of the formula (16), 0.11 g (0.5 mmol) of palladium acetate (Pd(OAc)$_2$), 12.2 g (0.12 mol) of triethylamine (Et$_3$N), and 100 ml of THF. Then, the autoclave was closed, followed by charging with ethylene until 50 bar and then heating with an oil bath at 120° C. After the reaction, the reaction liquid was transferred into a separating funnel, and hydrochloric acid was added thereto. The resulting aqueous layer was extracted several times with hexane. The resulting organic layers were combined together and washed with water and saturated brine. The obtained organic layer was dried by adding magnesium sulfate. Then, magnesium sulfate was removed by filtration, followed by vacuum distillation, thereby obtaining 11.8 g of a compound of the formula (18) (yield: 43.7%).

EXAMPLE 4

The second process was conducted to produce the target product, 4-HFA-ST (18), as shown by the following reaction scheme.

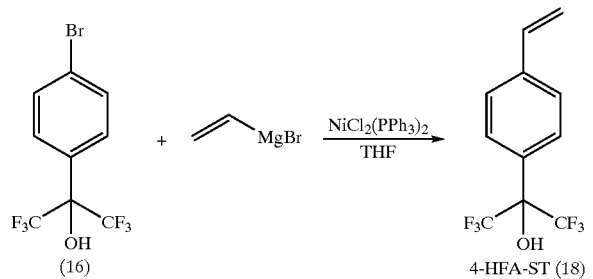

Under argon atmosphere, 110 ml of a THF solution (containing 14.4 g (0.11 mol) of vinyl magnesium bromide) were added at 0° C. to 240 ml of a THF solution (containing 32.3 g (0.1 mol) of a compound of the formula (16) and 0.65 g (1 mmol) of bis(triphenylphosphine)nickel chloride $NiCl_2(PPh_3)_2$), followed by stirring at 25° C. After the reaction, the reaction liquid was transferred into a separating funnel, and hydrochloric acid was added thereto. The resulting aqueous layer was extracted several times with hexane. The resulting organic layers were combined together and washed with water and saturated brine. The obtained organic layer was dried by adding magnesium sulfate. Then, magnesium sulfate was removed by filtration, followed by vacuum distillation, thereby obtaining 17.3 g of a compound of the formula (18) (yield: 65%).

EXAMPLE 5

The second process was conducted to produce the target product, 4-HFA-ST (18), as shown by the following reaction scheme.

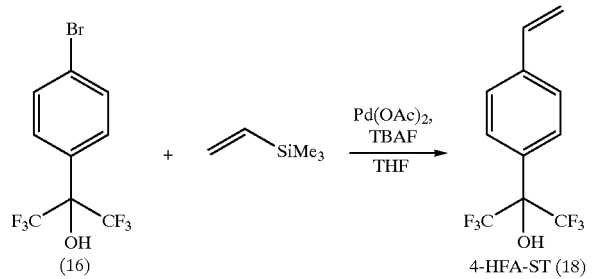

Under argon atmosphere, 300 ml of a THF solution (containing 30.1 g (0.3 mol) of trimethylvinylsilane and 61.3 g (0.3 mol) of tetrabutylammonium fluoride (TBAF)) were added to 200 ml of a THF solution (containing 64.6 g (0.2 mol) of a compound of the formula (16) and 2.31 g (2 mmol) of palladium acetate ($Pd(OAc)_2$)), followed by stirring under room temperature for 30 min and then conducting the reaction at 80° C. in a sealed tube. After the reaction, the reaction liquid was cooled down to room temperature, and the solvent was distilled away to obtain a crude product. This crude product was transferred into a separating funnel, and hydrochloric acid was added thereto. The resulting aqueous layer was extracted several times with hexane. The resulting organic layers were combined together and washed with water and saturated brine. The obtained organic layer was dried by adding magnesium sulfate. Then, magnesium sulfate was removed by filtration, followed by vacuum distillation, thereby obtaining 26.4 g of a compound of the formula (18) (yield: 49%).

EXAMPLE 6

The second process was conducted to produce the target product, 4-HFA-ST (18), as shown by the following reaction scheme.

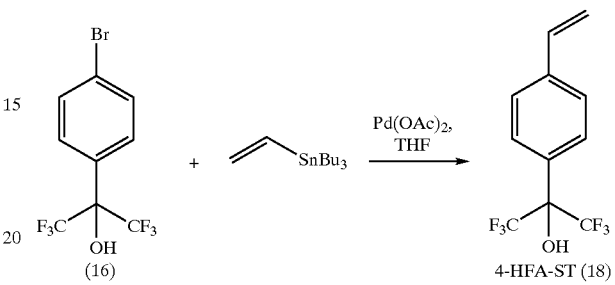

Under argon atmosphere, 95.1 g (0.3 mol) of tributyl vinyl tin were added to 200 ml of a THF solution containing 64.6 g (0.2 mol) of a compound of the formula (16) and 2.24 g (10 mmol) of palladium acetate ($Pd(OAc)_2$), followed by stirring under room temperature to conduct the reaction. After the reaction, the reaction liquid was transferred into a separating funnel, and hydrochloric acid was added thereto. The resulting aqueous layer was extracted several times with hexane. The resulting organic layers were combined together and washed with water and saturated brine. The obtained organic layer was dried by adding magnesium sulfate. Then, magnesium sulfate was removed by filtration, followed by vacuum distillation, thereby obtaining 30.2 g of a compound of the formula (18) (yield: 56%).

EXAMPLE 7

The second process was conducted to produce the target product, 4-HFA-ST (18), as shown by the following reaction scheme.

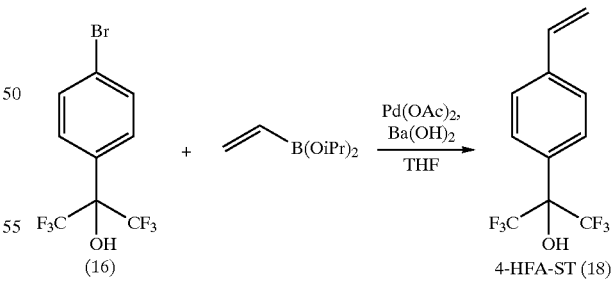

At first, the inside atmosphere of a four-necked flask (equipped with a reflux condenser, a thermometer, a dropping funnel, and a stirrer) was replaced with nitrogen, followed by adding 200 ml of a THF solution containing 32.3 g (0.1 mol) of a compound of the formula (16) and 18.7 g (0.12 mol) of isopropyl vinylborate. Then, 0.24 g (1 mmol) of palladium acetate ($Pd(OAc)_2$), 63.1 g (0.2 mol) of barium hydroxide octahydrate ($Ba(OH)_2 \cdot 8H_2O$), and 10 g of water were sequentially added, followed by stirring at reflux temperature to conduct the reaction. After the reaction, the reaction liquid was cooled down to room temperature, followed by adding hexane and water to obtain organic and aqueous layers. The organic layer was washed two times with water, and the solvent was distilled away under vacuum. To the obtained crude product, 200 ml of THF and 10.3 g of 75% sulfuric acid were added, followed by stirring at 20–30° C. After the reaction, water and hexane were added to obtain organic and aqueous layers. The organic layer was washed with water and saturated brine. The resulting organic layer was dried by adding magnesium sulfate. Then, magnesium sulfate was removed from the organic layer by filtration, followed by vacuum distillation, thereby obtaining 16.4 g of a compound of the formula (18) (yield: 61%).

EXAMPLE 8

In this example, the third process was conducted to produce the target product, 4-HFA-ST (18), as shown by the following reaction scheme.

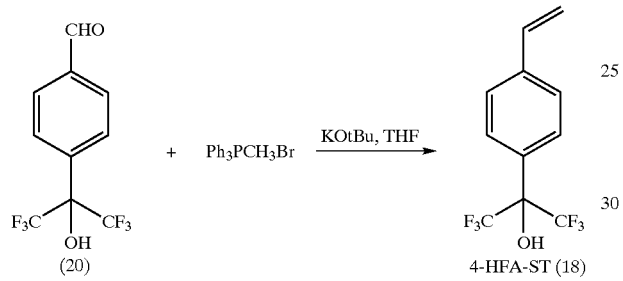

Under argon atmosphere, 132.3 g (0.15 mol) of phosphonium triphenylmethylbromide ($Ph_3PCH_3Br$) were dispersed in 200 ml of toluene. To the obtained suspension, 180 ml of a THF solution containing 20.2 g (0.18 mol) of potassium tert-butoxide (KOtBu) were added in a dropwise manner, followed by stirring at room temperature. When the resulting suspension of white color turned to have a yellow color, the reaction liquid was cooled down to $-10°$ C. Then, 100 ml of a THF solution containing 32.6 g (0.12 mol) of a compound of the formula (20) were added, followed by stirring at $-10°$ C. Then, 1N hydrochloric acid was added, followed by stirring at room temperature. With this, the reaction liquid was separated into aqueous and organic layers. The aqueous layer was extracted two times with hexane, and the organic layer was washed with sodium hydrogencarbonate, water and saturated brine. The total of the organic layers was dried by adding magnesium sulfate. Then, magnesium sulfate was removed by filtration, followed by vacuum distillation, thereby obtaining 10.1 g of a compound of the formula (18) (yield: 31%).

The entire disclosure of Japanese Patent Application No. 2002-183138 filed on Jun. 24, 2002, including specification, drawings, claims and summary, is incorporated herein by reference in its entirety.

What is claimed is:

1. A process for producing a fluorine-containing, polymerizable styrene monomer represented by the formula (2), the process comprising the steps of:

(a) reacting a compound represented by the formula (1) with a compound represented by the formula (3), in the presence of a metal catalyst, thereby producing a compound represented by the formula (4);

(b) reacting the compound represented by the formula (4) with a base, thereby producing a compound represented by the formula (5); and (c) reacting the compound represented by the formula (5) with hydrogen, in the presence of a metal catalyst and one of a phosphine and an amine, thereby producing the fluorine-containing, polymerizable styrene monomer represented by the formula (2),

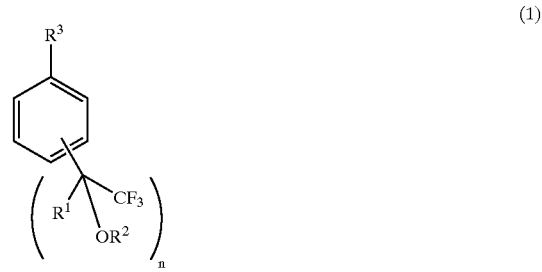

(1)

where $R^1$ a methyl group or trifluoromethyl group, $R^2$ is a hydrogen atom, an alkyl group, or an aryl group, each of the alkyl group and the aryl group independently having a carbon atom number of 1 to 25, independently having a straight-chain, branched or ring form, and independently and optionally having at least one of a fluorine atom, an oxygen atom, and a carbonyl bond, $R^3$ is a halogen atom or alkylsulfonyl group, and n is 1 or 2,

(2)

where $R^1$, $R^2$ and n respectively correspond to those of the formula (1),

(3)

where $R^4$ is $C(OH)R^5R^6$ or $SiR^7R^8R^9$ where each of $R^5$ to $R^9$ independently has a carbon atom number of 1 to 25, independently is an alkyl group or aryl group, and independently and optionally has, in place of a carbon atom, at least one of a hetero atom and a substituent, and where each of $R^5$ and $R^6$ independently and optionally contains a fluorinated alkyl group,

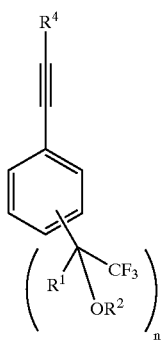
(4)

where $R^1$, $R^2$ and n respectively correspond to those of the formula (1), and $R^4$ corresponds to that of the formula (3),

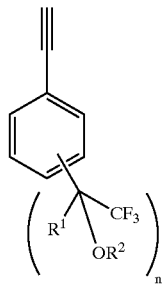
(5)

where $R^1$, $R^2$ and n respectively correspond to those of the formula (1).

2. A process according to claim 1, wherein the compound represented by the formula (4) is a compound represented by one of the formulas (6) to (9).

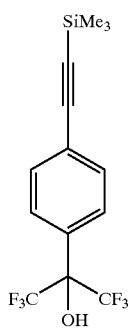
(6)

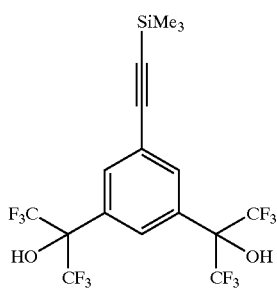
(7)

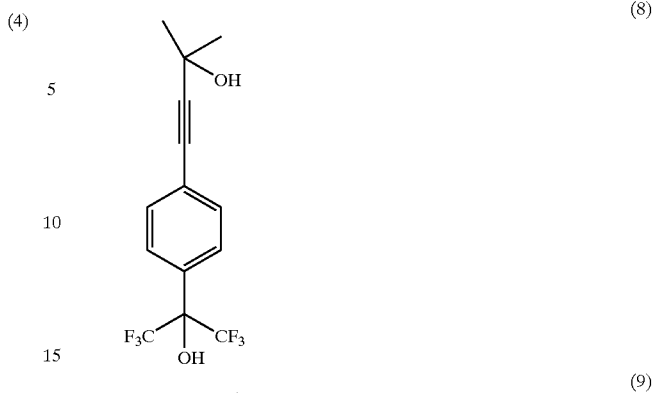
(8)

(9)

3. A process according to claim 1, wherein the compound represented by the formula (5) is a compound represented by the formula (10) or (11).

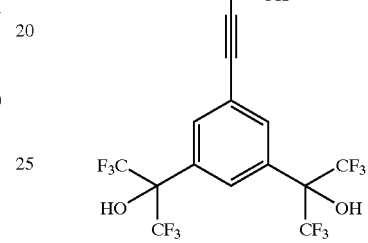
(10)

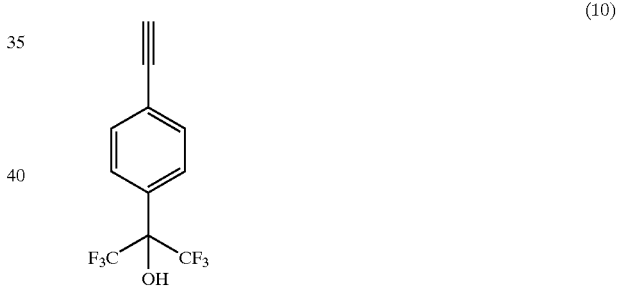
(11)

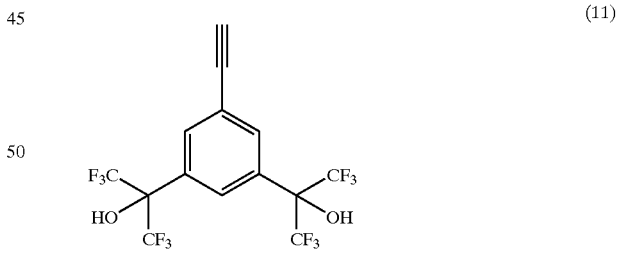

4. A process according to claim 1, wherein $R^1$ of the formula (1) is a trifluoromethyl group.

5. A process according to claim 1, wherein $R^2$ of the formula (2) is a hydrogen atom.

6. A process according to claim 1, $R^3$ of the formula (1) is a bromine atom, iodine atom, or trifluoromethylsulfonyl group.

7. A process according to claim 1, wherein the metal catalyst of the step (a) is selected from the group consisting of copper complexes, iron complexes, cobalt complexes, nickel complexes, rhodium complexes, palladium complexes, ruthenium complexes, platinum complexes, and combinations of these complexes.

8. A process according to claim 1, wherein the metal catalyst of the step (a) is a combination of a palladium complex and a copper complex.

9. A process according to claim 1, wherein the metal catalyst of the step (a) comprises a palladium complex, and wherein the step (a) is conducted in the presence of a phosphine.

10. A process according to claim 8, wherein the step (a) is conducted in the presence of a base.

11. A process according to claim 1, wherein the base of the step (b) is sodium carbonate or potassium carbonate.

12. A process according to claim 1, wherein the metal catalyst of the step (c) comprises a metal selected from the group consisting of palladium, platinum, rhodium, ruthenium, and nickel.

13. A process according to claim 12, wherein the metal catalyst of the step (c) comprises palladium and one of barium sulfate and calcium carbonate.

14. A compound represented by one of the following formulas (6) to (11), which is an intermediate in the process according to claim 1.

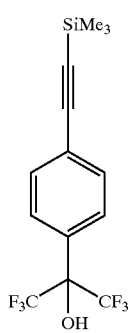
(6)

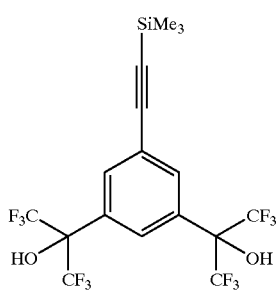
(7)

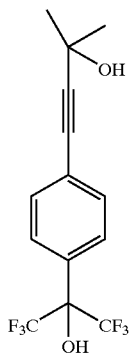
(8)

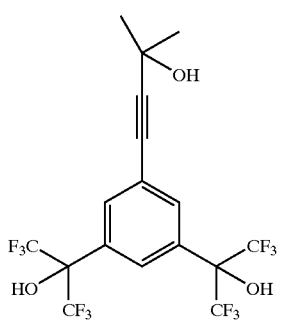
(9)

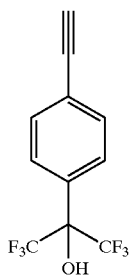
(10)

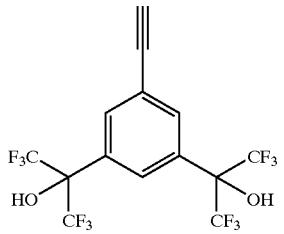
(11)

* * * * *